United States Patent [19]

Sanders et al.

[11] Patent Number: 5,391,168
[45] Date of Patent: Feb. 21, 1995

[54] DEVICE FOR CORRECTING THE SHAPE OF THE HUMAN SPINAL COLUMN AND/OR FOR FIXING THE HUMAN SPINAL COLUMN

[75] Inventors: M. M. Sanders, Bodegraven; J. C. Cool, Pijnacker; A. G. Veldhuizen, Eelde; P. Timmerman, Enscheds; G. J. Bazuin, Zwolle; J. J. N. Best, Nunspeet, all of Netherlands

[73] Assignee: Acromed B.V., Netherlands

[21] Appl. No.: 41,248

[22] Filed: Apr. 1, 1993

[30] Foreign Application Priority Data

Apr. 1, 1992 [NL] Netherlands .................. 9200612

[51] Int. Cl.⁶ .............................................. A61B 17/58
[52] U.S. Cl. .................................................. 606/61
[58] Field of Search ................ 606/60, 61, 72, 74

[56] References Cited

U.S. PATENT DOCUMENTS

| | | | |
|---|---|---|---|
| 4,611,582 | 9/1986 | Duff | 606/61 |
| 5,181,917 | 1/1993 | Rogozinski | 606/61 |

FOREIGN PATENT DOCUMENTS

| | | |
|---|---|---|
| 0470660 | 2/1992 | European Pat. Off. |
| 7205928 | 11/1973 | Netherlands |
| 9119469 | 12/1991 | WIPO |

*Primary Examiner*—Tamara L. Graysay
*Attorney, Agent, or Firm*—Larson and Taylor

[57] ABSTRACT

The invention relates to a device for correcting the shape of the human spinal column (S) and/or for fixing the human spinal column (S), comprising at least one rod (2) extending in a longitudinal direction, in particular a rod made of material with a shape-memory, and at least one attachment element (3, 13) comprising two hooks (4, 14), a bridge (5, 17) and rod connecter (6), the bridge (5, 17) forming the connection between the hooks (4, 14), and the rod connecter (6) being adapted for detachably connecting the attachment element (3, 13) with the rod, wherein, according to the invention, the hooks (4, 14) substantially extend in a plane extending perpendicularly to the rod (2), the respective hooks (4, 14) being detachably connected with the bridge (5, 17) through a first end (4a, 15a) and being directed toward each other through second, hook-shaped, free ends (4b, 16a).

19 Claims, 6 Drawing Sheets

DEVICE FOR CORRECTING THE SHAPE OF THE HUMAN SPINAL COLUMN AND/OR FOR FIXING THE HUMAN SPINAL COLUMN

The present invention relates to a device for correcting the shape of the human spinal column and/or for fixing the human spinal column, comprising at least one rod extending in a longitudinal direction, in particular a rod made of material with a shape-memory, and at least one attachment element comprising two hooks, a bridge and rod connecting means, the bridge forming the connection between the hooks, and the rod connecting means being adapted for detachably connecting the attachment element with the rod.

Such a device is disclosed in European patent application no. 0 470 660 and is intended for correcting serious deformations of the shape of the spinal column, in particular lateral curvature (scoliosis) of the spinal column and the accompanying axial turning of the vertebrae. The device proposed in the European patent application referred to utilizes a rod with a shape-memory. Examples of materials having such a shape-memory include Ti-Ni alloys. When such materials are plastically deformed below a given "transition temperature", they will adopt their original shape again upon increase of the temperature above this transition temperature. With a rod of appropriately chosen dimensions, this holds for bending as well as torsion. However, when the rod, in its deformed condition, is fixed and unable to adopt its original shape, it will exert a force on the fixing provision in the direction of its original shape. These properties are used advantageously in the device proposed in the European patent application referred to. The rod exerts a force on the deformed spinal column for a prolonged time. Since the spinal column has viscoelastic properties, the deviations in the shape of the spinal column will be corrected entirely after a certain lapse of time. Even in the case of serious deformations, this lapse of time is such (approx. 3-4 weeks) that the correction will have been completed by the time the vertebrae begin to fuse (i.e. grow together while stiffening).

However, a problem of the device proposed in the European patent application referred to is that the attachment elements which form the fixing provision for the rod and which connect the rod with the respective vertebrae do not fully satisfy the requirements set. Both the connection of the known attachment element with a vertebra and the connection of the rod with the attachment element constitute a problem in the known device.

The connection of the known attachment element with a vertebra is formed by two hooks which each engage under a process of a vertebra or which engage the underside of a vertebra in the manner of a lamina hook between the vertebrae. Such an attachment element is fixed only in that the tension in the rod presses the attachment elements against the respective vertebrae. A loose attachment element, i.e., an attachment element that has not been connected to the rod yet, does not remain in position. Due to the fact that the spinal column, when a rod with a shape-memory is used, undergoes a substantial change in shape after a lapse of time and due to the fact that the direction and the magnitude of the forces exerted on the attachment elements by the rod change after a lapse of time, the connection between the attachment elements and the vertebrae is not a connection that is secure for a prolonged time.

The object of the present invention is to provide a device for correcting the shape of and/or for fixing the human spinal column, which obviates the problems described hereinabove.

To that end, the device of the present invention, include hooks that substantially extend in a plane extending perpendicularly to the rod, the respective hooks being detachably connected with the bridge through a first end and being directed towards each other through second, hook-shaped, free ends.

In such a device, the attachment elements are designed for lateral engagement around the vertebral arch. Before such an attachment element is mounted on the vertebral arch, first the spinous process of the relevant vertebra must be removed in part or in whole. Next, the hooks are hooked to the vertebral arch via the intervertebral foramen, whereafter the bridge is mounted, this bridge interconnecting the two hooks. Next, the hooks, together with the bridge, can be fixed to the relevant vertebra with suitable fixing means, such as for instance studs, nuts and/or the like. Thus, the attachment elements can be rigidly fixed to the respective vertebrae without the rod being mounted.

Although the device is particularly suitable for applications where use is made of rods of a material having a shape-memory, i.e., for applications where the shape of the spinal column is to be corrected, the device can also be employed using rods made of normal material.

When the hooks are connected with the bridge, a tensile force is exerted on the hooks in ventrodorsal direction, this tensile force being transmitted to the inside of the vertebral arch. The bridge of the attachment element is drawn against the outside of the vertebral arch, thus exerting a force on the vertebral arch in dorsoventral direction. Accordingly, with the attachment elements of the device according to the invention, a good fixation of the attachment elements relative to the respective vertebrae is obtained, at any rate in dorsoventral and ventrodorsal direction.

In order to ensure a good fixation of the attachment elements relative to the respective vertebrae in lateral direction as well, it is particularly advantageous when, in further elaboration of the invention, the bridge consists of two or more bridge members, each bridge member being connected with an adjacent bridge member for hinging movement about a longitudinal line, the bridge members located at the lateral free ends each carrying one of the two hooks. In a preferred embodiment of the device with attachment elements of such a design, the bridge consists of two bridge members interconnected for hinging movement about a longitudinally directed line, the hinge line being located substantially in the middle between the two hooks.

When being mounted, an attachment element of such design will clamp itself onto the vertebral arch in a manner comparable to the manner of a pulley puller clamping itself onto a pulley. During mounting, the hinged bridge will hinge about the vertebral arch, so that the hook-shaped ends of the hooks move toward each other and are clamped onto the sides of the vertebral arch.

According to a further elaboration of the invention, the hingedly interconnected bridge members may be interconnected by means of a hinge pin. Such a hinged joint is simple and can therefore be realized at a low cost price. It is also possible, however, for the hingedly interconnected bridge members to be interconnected via a plastically/elastically deformable member. This offers the advantage that the bridge consisting of a plurality of bridge members can be manufactured in a particular preferred position. Such a preferred position can for instance be the bent position. When the bridge is to be mounted, it is straightened with a pair of tongs and fitted over the hooks. When the bridge is released, it assumes the bent position, the second, hook-shaped ends of the hooks thereby being forced towards each other in lateral direction. This property can be used particularly advantageously when, in accordance with a further embodiment of the invention, the plastically/elastically deformable member is made of a material with a shape-memory which, in mounted condition, adopts a bent position.

In a normal pulley puller, at the hinge, a push pin is arranged which pushes against an end surface of the shaft that carries the pulley. As the pulley is pulled loose, i.e., as the push pin is tightened against the end surface, the height of the pulley puller increases. Since the operation of the above-described attachment element is comparable to that of a normal pulley puller, this attachment element would have a substantial overall height in mounted condition if the clamping force were generated by a push pin at the hinge.

In order to circumvent this drawback while still utilizing the particularly advantageous principle of the pulley puller, the attachment element is characterized, according to a further elaboration of the invention, in that the hooks are mounted in passages in the bridge members so as to be restrained from rotation, the hooks being slidable relative to the bridge members in the direction of the passage and the first ends of the hooks each being threaded for cooperation with a nut. Thus, when this attachment element is being mounted, the hinge is not pushed up by a push pin, as is usual, but the ends of the bridge members remote from the hinge are pulled down by tightening the respective nuts fitted on the first ends of the hooks. As the nuts are tightened, the hooks, of course, should not turn relative to the arch. This is prevented in that the hooks are mounted in the passages in the bridge members so as to be restrained from rotation.

According to another further elaboration of the invention, not operating in accordance with the principle of the pulley puller, the hooks may each consist of two detachably interconnected members, one member being formed by a stud, which, via a threaded throughbore in a second, hook-shaped member, is connected therewith, whilst, in mounted condition, one end of the stud extends in the direction of the free end of the hook of the second, hook-shaped member and the other end of the stud reaches through slotted holes provided in the bridge, these slotted holes allowing a displacement of the hooks towards and away from each other as the hooks are mounted on the bridge.

An attachment element of such design offers the advantage that it can be manufactured economically and that one standard model is applicable to vertebrae of widely varying dimensions. The stud, which, in mounted condition, extends in the direction of the free end of the hook, enables the hooks to be secured to the arch before mounting the bridge. This is of particular importance during mounting, since this enables the orthopedist to keep his hands free for mounting the bridge.

Here, it is particularly advantageous when, in accordance with a further embodiment of the invention, in mounted condition, the second, hook-shaped members are arranged so as fit in a slot in the bridge. The slot prevents rotation of the hook-shaped members relative to the bridge and ensures that during mounting any couples exerted on the hooks are not taken up by the vertebral arch.

In both further elaborations of the invention described above, the rod connecting means are of such design that the forces and couples exerted on the relevant attachment element are transmitted to the rod in question in a mounted condition thereof. This is also the case in the attachment elements disclosed in the European patent application referred to. In these known attachment elements, the rod connecting means are formed by rectangular recesses extending in longitudinal direction, opening towards the rear, into which the rectangular rod fits accurately. Rod connecting means of such design present the problem that, when the rod is to be mounted, the rod must already have the exact desired shape before it is mounted. In particular with regard to the axial twist or torsion of the rod, this is not easy to realize.

In order to solve this problem, according to a further embodiment of the invention, the rod connecting means are designed to permit rotation of the rod in question about its longitudinal axis in a semi-mounted condition thereof.

Here, it is particularly advantageous when, according to a further embodiment of the invention, the rod, in mounted condition, conformably abuts the rod connecting means through at least a part of its circumference, the rod having a cross-section, at least at that circumferential part, that does not allow rotation of the rod relative to the attachment element. Such a conformably abutting fixation ensures that the rod adopts the proper rotational position upon the transition from the semi-mounted to the fully mounted condition. During the transition from the semi-mounted condition to the fully mounted condition, it is particularly advantageous, in the case where a rod made of memory material is used, when the temperature of the rod is still below the transition temperature.

According to a further elaboration of the invention, rod connecting means that can be manufactured simply and economically are formed by two pins of substantially constant diameter, located on the side of the bridge or bridge members remote from the hook-shaped ends, these pins each comprising a first and a second threaded end, the first ends each being mounted in substantially parallel, threaded bores in the bridge or one of the two bridge members, whilst the rod can be received to fit between the two pins and, in mounted condition, is locked between the bridge or one of the bridge members and a cover plate which can be attached to the pins by means of nuts, this cover plate comprising two holes corresponding with the pins.

The possibility of rotation of the rod in the semi-mounted condition is realized, in accordance with a further elaboration of the invention, in that, behind the threaded portion of the first end of each pin, a portion is provided with a smaller diameter such that the rod can rotate about its longitudinal axis when it is disposed in the semi-mounted position between the two pins at the respective portions of smaller diameter, whilst the portion of smaller diameter, at least through a part thereof that is proximal to the second end, merges gradually into the portion of constant diameter, the diameter of this portion of constant diameter being such that the rod cannot rotate about its longitudinal axis when it is disposed in the mounted position between the two pins at the respective portions of constant diameter.

The operation of the rod connecting means so designed is as follows: the first ends of the pins are partly screwed into the parallel bores in one of the bridge members, the portion of smaller diameter being disposed outside the bridge or the bridge member. Next, the rod is fitted between the pins at the portion of smaller diameter. Next, the cover plate is fitted over the pins and the nuts are screwed onto the second ends of the pins. As the nuts are tightened, the cover plate is pushed against the rod. The nuts are tightened until they reach the end of the thread at the second end of the pins and can be screwed no further. Then the nuts are turned further, so that the pins turn with them and move further into the parallel bores. Thus, the respective portions of smaller diameter of the pin disappear into the bores and the rod is pressed via the gradual transition from the portion of smaller diameter to the portion of constant diameter into the portion of constant diameter. During this operation, the rod adopts its final rotational position. Rod connecting means of such design accordingly offer the advantage that the rod need not follow the curvature and twist of the spinal column very accurately yet before it is mounted. The curvature and twist of the rod can still be adjusted during mounting. Of course, it is important here that if the rod is made of memory material, the rod, when being adjusted, has a temperature below the transition temperature.

In order to properly distribute the clamping forces exerted on the arch and to increase the abutting surface of the attachment elements, the bridge or one of the bridge members may, on the side remote from the rod, be provided with abutting projections with vertebra contact surfaces.

To clarify the present invention, three embodiments of the device will now be described, by way of example only, with reference to the accompanying drawings.

Figure 1:
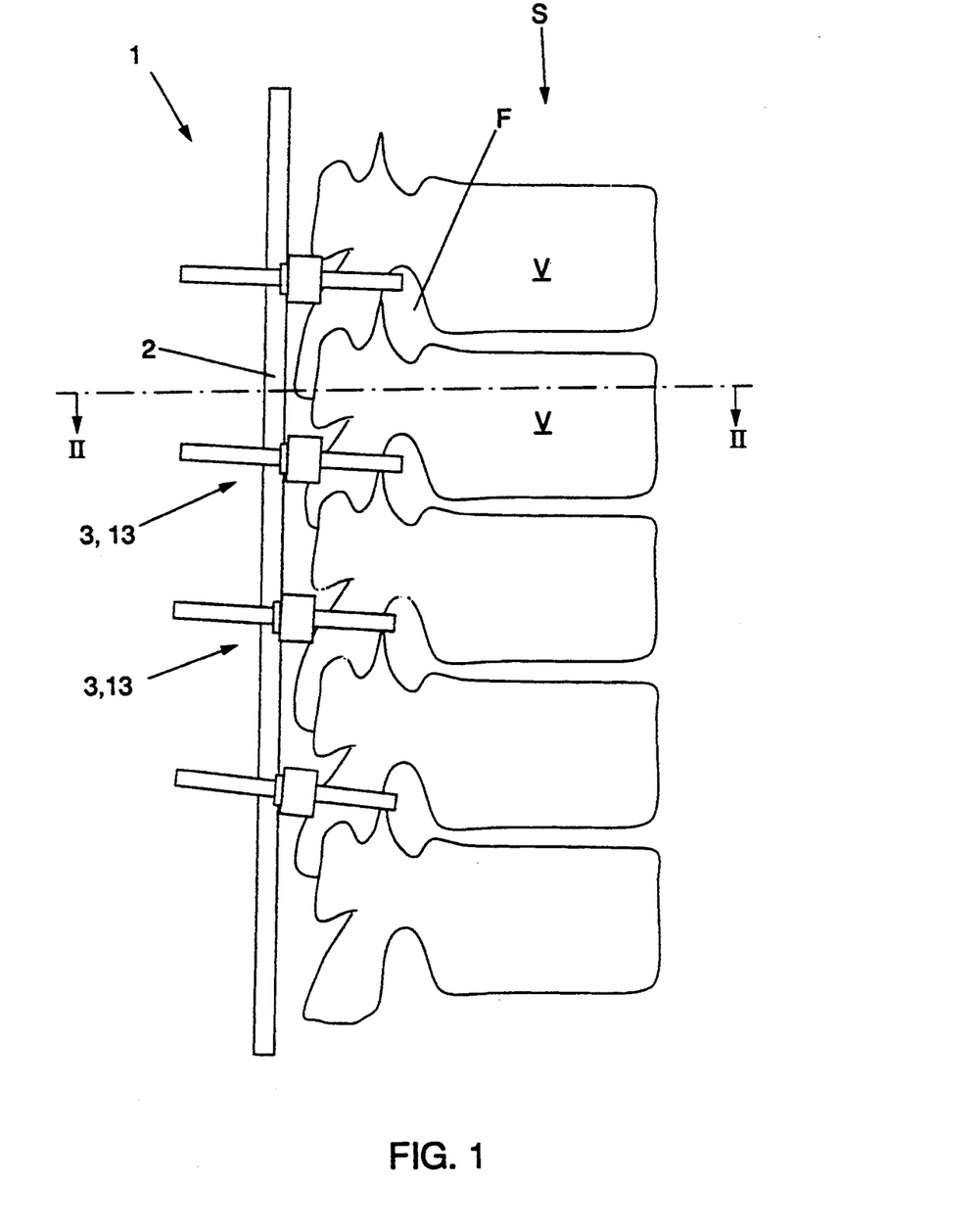
FIG. 1 is a schematic side elevation taken on the line I—I of FIG. 2 of the device mounted on a spinal column.
Figure 2:
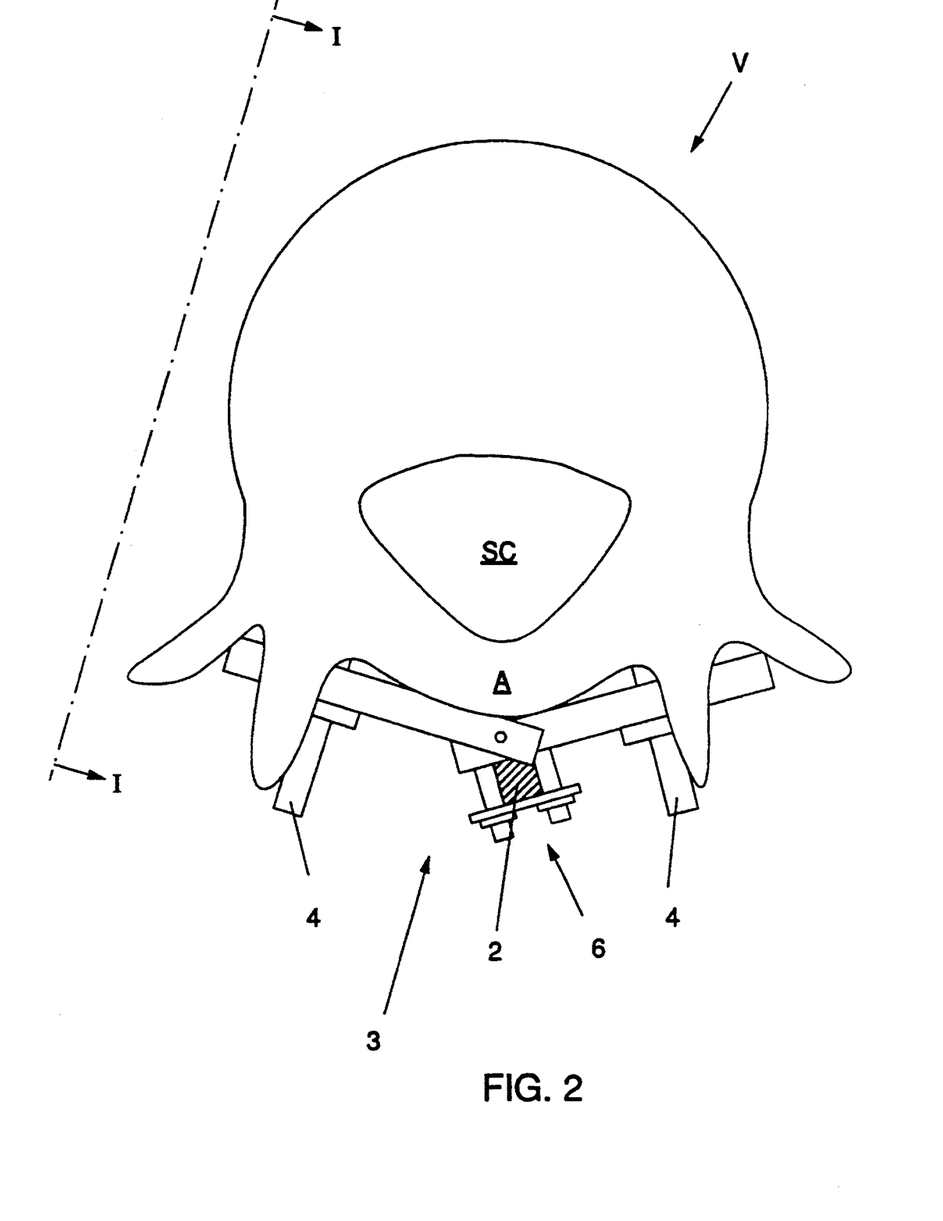
FIG. 2 is a schematic sectional view of the spinal column with the device mounted thereon, taken on line II—II of FIG. 1.

The schematic side elevation of FIG. 1 of an embodiment of the device 1 for correcting the shape of the spinal column S and/or for fixing the spinal column S, shows the manner of attachment of the device 1 to a spinal column S. The spinal column S is made up of a plurality of vertebrae V. Located between two vertebrae V arranged above each other, adjacent the vertebral arch (FIG. 2), is an opening F, to be referred to as intervertebral foramen, through which branches of the spinal cord leave the spinal canal SC. The device 1 is attached to the rear of the spinal column S and comprises a rod 2 extending in longitudinal direction, made of material with shape-memory and attachment elements 3 or 13. The attachment elements 3 or 13 (FIGS. 3-6 and FIGS. 7-9) comprise two hooks 4 and 14, respectively, a bridge 5 and 17, respectively, and rod connecting means 6. The bridge 5 and 17, respectively, constitutes the connection between the hooks 4 and 14, respectively, and the rod connecting means 6 are designed for detachably connecting the attachment element 3 and 13, respectively, with the rod 2. According to the present invention, the device 1 is characterized in that the hooks 4 and 14, respectively, substantially extend in a plane perpendicular to the rod 2, the respective hooks 4 and 14 being detachably connected with the bridge 5 and 17, respectively, through a first end 4a and 15a, respectively, and being directed towards each other through second, hook-shaped free ends 4b and 16a, respectively. Such mutually facing hook-shaped free ends 4b, and 16a, respectively, are suitable for engaging the vertebral arch A via the intervertebral foramen F. Before an attachment element 3 or 13 is fixed onto the vertebra V, first the spinous process (not shown) of the relevant vertebra V must be removed in part or in whole. The connection of the attachment elements 3 or 13 to the vertebrae V does not weaken the vertebrae and is such that the hooks do not narrow the spinal canal SC, which is clearly shown in FIG. 2.

Figure 3:
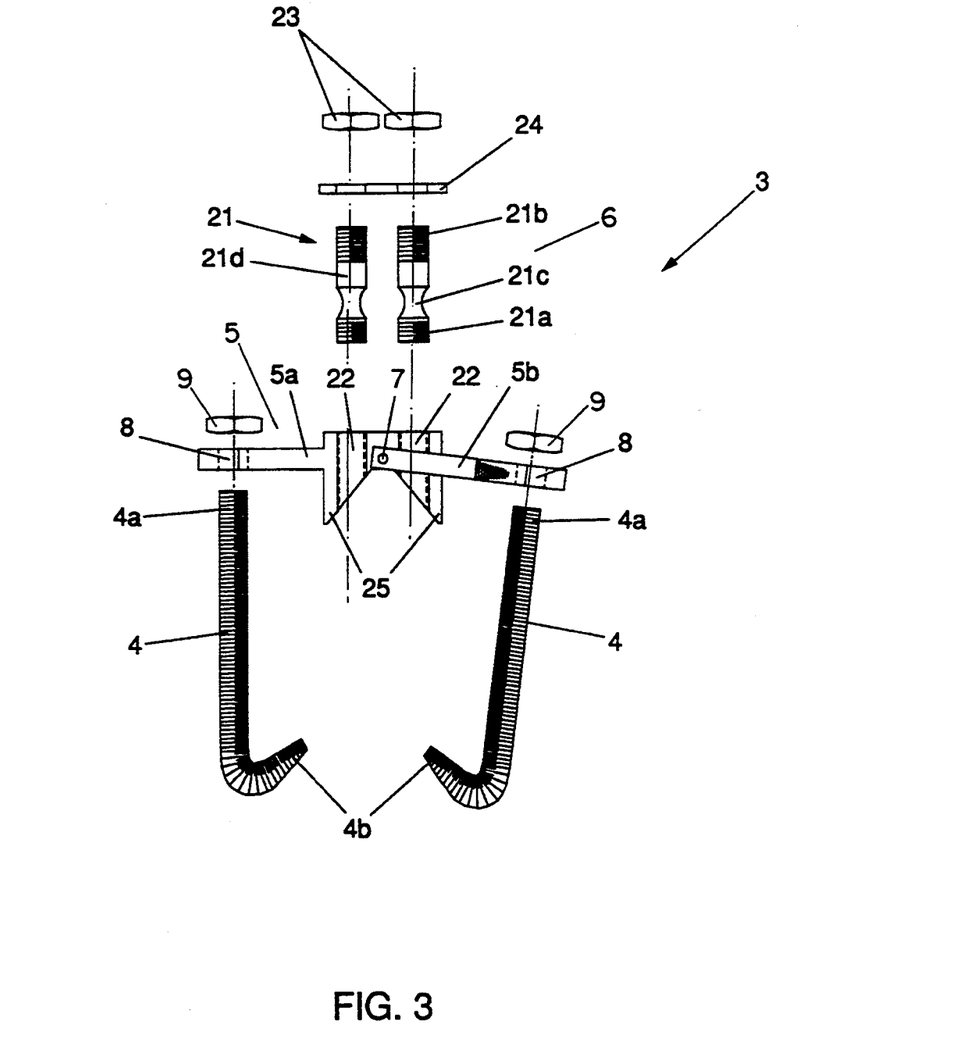
FIG. 3 is an exploded view of a first embodiment of an attachment element.
Figure 4:
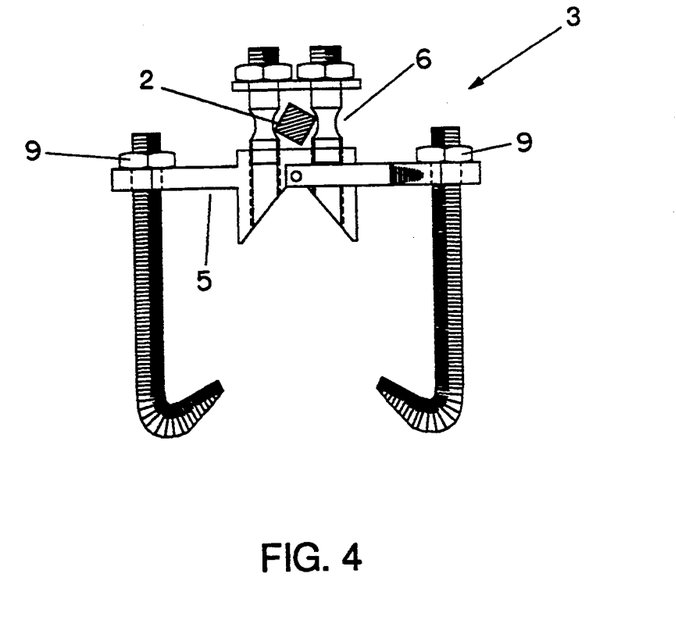
FIG. 4 shows the attachment element depicted in FIG. 3, with the rod in semi-mounted condition.
Figure 5:
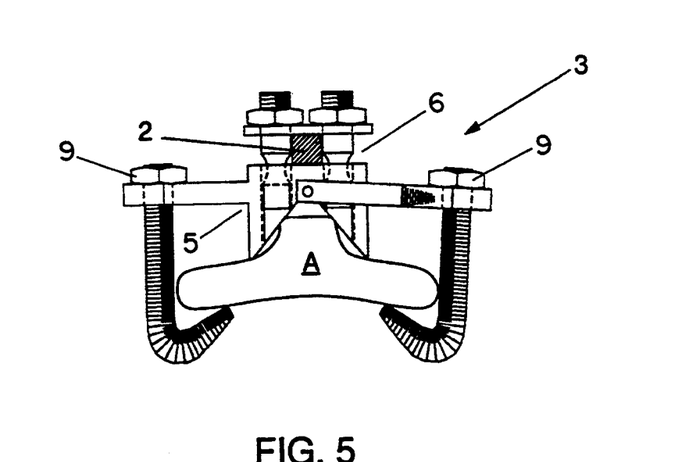
FIG. 5 shows the attachment element depicted in FIG. 3, with the rod in fully mounted condition.
Figure 6:
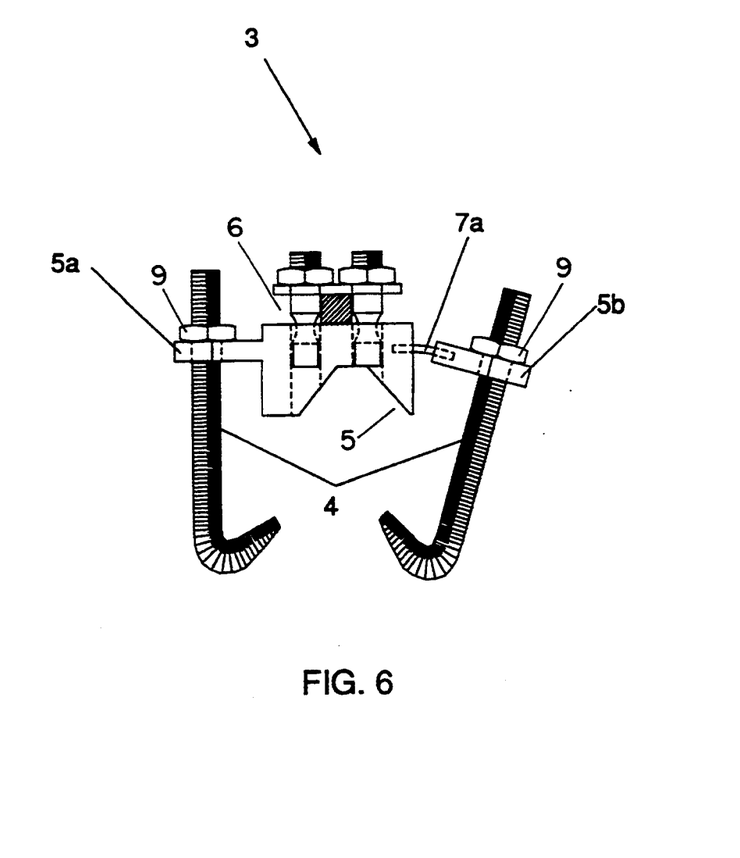
FIG. 6 shows a second embodiment of an attachment element with the bridge members being interconnected by means of a plastic/elastic hinge.

FIGS. 3-6 show a first and a second embodiment of an attachment element 3. The principal feature of the attachment element 3 shown in these drawings is that the bridge 5 consists of two bridge members 5a and 5b, respectively, interconnected for hinging movement about a longitudinally directed line 7, this hinge line 7 being located substantially in the middle between the two hooks 4, and each bridge member 5a and 5b, respectively, carrying one of the two hooks 4. The hooks 4 are mounted so as to be restrained from rotation in passages 8 provided in the bridge members 5a and 5b, respectively. The hooks 4 are slidable relative to the bridge members 5a and 5b, respectively, in the direction of the passage 8, and the first ends 4a of the hooks 4 are each provided with thread for cooperation with a nut 9. In this embodiment, the hooks 4 are restrained from rotation in the passages 8 in that the stem of the hooks 4 comprises a flat side (not shown) and in that the passages 8 comprise a flat wall portion (not shown) corresponding with this flat side. After the attachment elements 3 have been mounted on the respective vertebrae V, the first ends 4a of the hooks 4 are cut off, as shown in FIG. 5.

The hingedly interconnected bridge members 5a and 5b, respectively, can be interconnected by means of a hinge pin 7 (see FIGS. 3-5). It is also possible, however, for the hingedly interconnected bridge members 5a and 5b, respectively, to be interconnected via a plastically/elastically deformable member 7a (see FIG. 6). Such a plastically/elastically hinge 7a gives the advantage that the bridge 5a and 5b, respectively, can be manufactured in a particular preferred position. Such a preferred position can for instance be the bent position. During mounting, the bridge 5a and 5b, respectively, is then straightened with a pair of tongs and fitted over the hooks 4. When the bridge 5a, 5b is released, it adopts the bent position, the two hook-shaped ends 4b of the hooks 4 thereby being pushed toward each other in lateral direction. This property can be utilized particularly advantageously when the plastically/elastically deformable member 7a is made of material with a shape-memory, which adopts a bent position in the mounted condition.

Figures 7, 8:
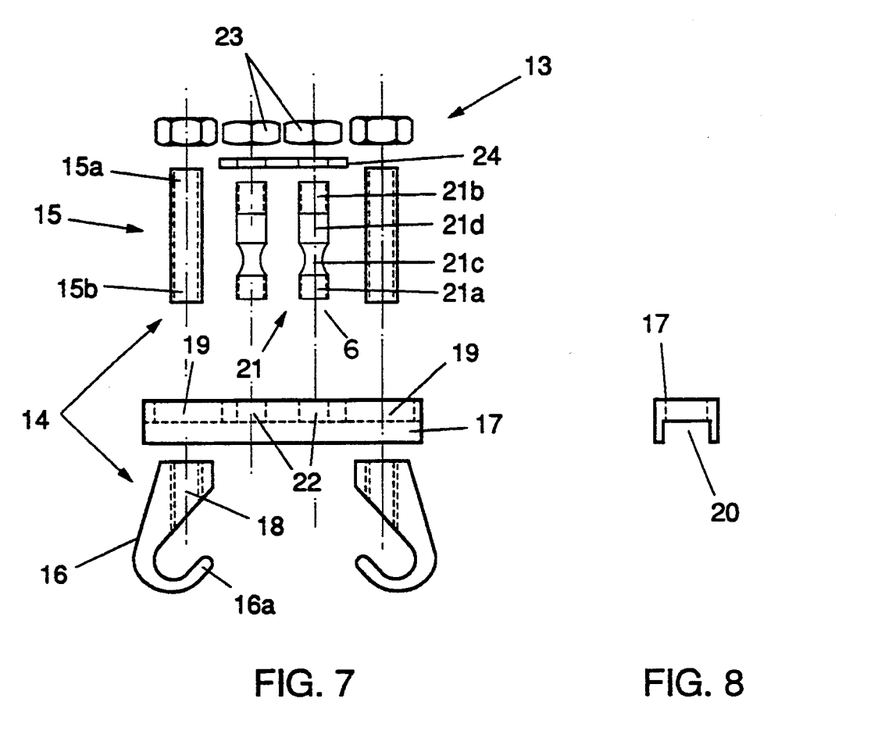
FIG. 7 is an exploded view of a third embodiment of an attachment element.
FIG. 8 is a side elevation of the bridge of the attachment element shown in FIG. 7.
Figure 9:
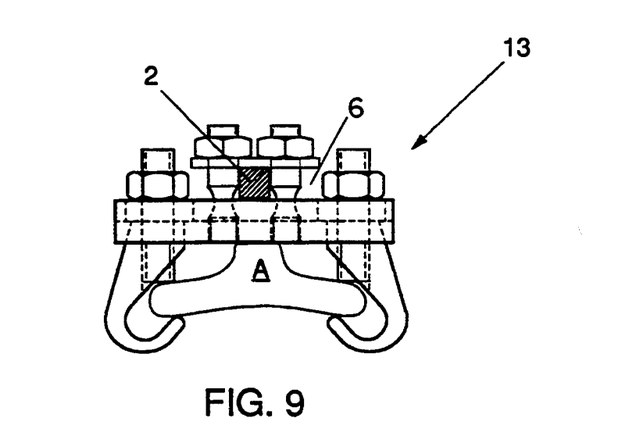
FIG. 9 shows the embodiment depicted in FIG. 7 in fully mounted condition.

FIGS. 7-9 show a third embodiment of an attachment element 13, where, likewise, the hooks 14 extend substantially in a plane extending perpendicularly to the rod 2, and the respective hooks 14 are detachably connected with the bridge 17 through a first end 15a and are directed toward each other through second, hook-shaped free ends 16a. This embodiment is characterized in that the hooks 14 each consist of two detachably interconnected members, a first member 15 being formed by a stud 15, which is connected to a second, hook-shaped member 16 via a threaded throughbore 18 provided therein. In mounted condition, one end 15b of the stud 15 extends in the direction of the free end 16a of the hook of the second, hook-shaped member 16, whilst another end 15a of the stud 15 reaches through slotted holes 19 provided in the bridge 17, these slotted holes permitting displacement of the hooks 14 away from and toward each other while the hooks 14 are being mounted on the bridge 17.

In order to prevent the hooks 14 from turning relative to the bridge 17 while the attachment element 13 is being mounted, the second, hook-shaped members 16, in mounted condition, are located in a slot 20 in the bridge 17.

All attachment elements 3 and 13, respectively, shown in FIGS. 3-9, are equipped with rod connecting means 6, which are so designed that the forces and couples exerted on the relevant attachment element 3 or 13 are transmitted to the rod 2 in a mounted condition thereof (see FIG. 5 and FIG. 9) and, further, are so designed that the rod connecting means 6 permit rotation of the rod 2 about a longitudinal axis thereof in a semi-mounted condition of the rod 2 (see FIG. 4).

In order to obtain the proper rotational position of the rod 2 at the transition from the semi-mounted condition to the fully mounted condition, it is particularly advantageous when the rod 2, in mounted condition, conformably abuts the rod connecting means 6 through at least a part of its circumference. In the embodiments shown, this is realized in that the rod 2 has a square cross-section of approx. 6×6 mm. It will be clear, however, that this cross-section may also be elliptic, rectangular or polygonal.

The rod connecting means 6 are formed by two pins 21 of substantially constant diameter, located on the side of the bridge 17 or bridge members 5a and 5b, respectively, remote from the hook-shaped ends 4b and 16a, respectively. The pins 21 each comprise a first threaded end 21a and a second threaded end 21b. The first ends 21a of the respective pins 21 are mounted in substantially parallel threaded bores 22 in the bridge 17 or one of the two bridge members 5a. The rod 2 can be received to fit between the two pins 21, and the rod 2, in mounted position, is locked between the bridge 17 or one of the bridge meanders 5a and a cover plate 24, which can be secured to the pins with nuts 23, this cover plate 24 comprising two holes (not shown) corresponding with the pins 21.

Provided behind the threaded portion of the first end 21a of each pin 21 is a portion 21c having a smaller diameter such that the rod 2 can rotate about its longitudinal axis when, in semi-mounted condition, it is located between the two pins 21 at these respective portions 21c of smaller diameter (FIG. 4). The portion 21c of smaller diameter gradually merges into the portion of constant diameter 21d. This portion 21d has a diameter such that the rod 2 cannot rotate about its longitudinal axis when, in mounted position (FIG. 5), it is located between the two pins 21 at the respective portions of constant diameter 21d.

Such rod connecting means 6 offer the great advantage that the rod 2, prior to mounting, need not be pre-formed very accurately yet, with regard to torsion in particular. This advantage is of particular importance now that the rod 2 is only fixed in the attaching means 3 or 13 after the attaching means 3 or 13 have been secured to the spinal column S.

It will be clear, however, that rod connecting means of a different type can be used as well. For instance, the rod connecting means used in the European patent application referred to could be used. However, these known rod connecting means, which are formed by rectangular recesses extending in longitudinal direction in the attachment elements, do not yield the important advantage described hereinabove.

The attachment element 3 shown in FIGS. 3-6 comprises abutting projections 25 provided with vertebra contact surfaces. These abutting projections 25 distribute the pressure exerted on the arch A by the bridge 17 or bridge members 5a and 5b, respectively, and yield improved abutment of the attachment element 3 against the vertebrae V. As a consequence, the chances of displacement or rotation of the attachment elements 3 relative to the vertebrae V is limited to a minimum. Naturally, the embodiment shown in FIGS. 7-9 may also be provided with such abutting projections.

It will be clear that the present invention is not limited to the embodiments described, but that various modifications are possible within the framework of the invention. For instance, the rod is depicted as being located in the middle between the two hooks (see FIGS. 3-5 and 7-9), but it will be clear that they may also be located close to a lateral end of the bridge or one of the bridge members (see FIG. 6).

We claim:

1. A device for correcting the shape of the human spinal column and/or for fixing the human spinal column, comprising at least one rod extending in a longitudinal direction, and at least one attachment element comprising two hooks, a bridge, and rod connecting means, the bridge forming the connection between the hooks, and the rod connecting means being adapted for detachably connecting the attachment element with said at least one rod, wherein the hooks substantially extend in a plane extending perpendicularly to said at least one rod, the respective hooks being detachably connected with the bridge through a first end and being directed toward each other through second, hook-shaped, free ends.

2. A device according to claim 1, wherein the bridge comprises two or more bridge members, each bridge member being connected with an adjacent bridge member by hinging means for allowing hinging movement about a longitudinal line, said two hooks being located at opposite lateral free ends of said bridge.

3. A device according to claim 2, wherein the hinging means comprises a hinge pin.

4. A device according to claim 2, wherein the hinging means comprises a plastically/elastically deformable member.

5. A device according to claim 4, wherein the plastically/elastically deformable member is made of material with a shape-memory and has a bent shape.

6. A device according to claim 2, wherein one of said two hooks are mounted in a first passage in one of said bridge members and another of said two hooks is mounted in a second passage in another of said bridge members so as to restrain said hooks from rotating, the hooks being slidable relative to the bridge members through the passage, and the first ends of the hooks each being threaded for cooperation with a nut.

7. A device according to claim 1, wherein the bridge consists of two bridge members interconnected by hinging means for allowing hinging movement about a longitudinally directed line, one of said two hooks being located at a lateral free end of a first one of said two bridge members and another of said two hooks being located at a lateral free end of a second one of said two bridge members, the longitudinally directed line being located substantially centrally between the two hooks.

8. A device according to claim 1, wherein the hooks each consist of two detachably interconnected members, a first member thereof being formed by a stud, which, via a threaded through bore in a second, hook-shaped member, is connected therewith, while, when said attachment element is mounted on said at least one rod, one end of the stud extends in the direction of the free end of the hook of the second, hook-shaped member and another end of the stud reaches through slotted holes provided in the bridge, said slotted holes allowing a displacement of the hooks towards and away from each other as the hooks are being mounted on the bridge.

9. A device according to claim 8, wherein the second, hook-shaped members fit in a slot in the bridge.

10. A device according to claim 1, in which the rod connecting means comprises means for transmitting forces and couples exerted on said at least one attachment element to said at least one rod when said attachment element is secured on said at least one rod, wherein the rod connecting means further comprises means for permitting rotation of said at least one rod about a longitudinal axis of said at least one rod when said attachment element is mounted on said at least one rod but before said attachment element is secured to said at least one rod.

11. A device according to claim 10, wherein, when said attachment element is secured on said at least one rod, at least two opposite sides of said at least one rod conformably abut the rod connecting means, the abutment preventing rotation of said at least one rod relative to the attachment element.

12. A device according to claim 10, wherein the rod connecting means comprises two pins, located on a side of the bridge remote from opposite the hook-shaped ends, said pins each comprising a first threaded end and a second threaded end having a constant diameter portion, the first ends each being mounted in substantially parallel threaded bores in the bridge, said at least one rod can fit between the two pins and, when said attachment element is secured on said at least one rod, said at least one rod is locked between the bridge and a cover plate which is secured to the second threaded end of the pins with nuts, said cover plate comprising two holes corresponding with the second threaded end of the pins.

13. A device according to claim 12, wherein between the first threaded end and the second threaded end of each pin, a portion of smaller diameter is provided such that said at least one rod can rotate about a longitudinal axis of said at least one rod when said attachment element is mounted on said at least one rod and said at least one rod is between the two pins at said respective portions of smaller diameter, each portion of smaller diameter, at least partially is proximal to the first threaded end, merges gradually into the portion of constant diameter, the diameter of each portion of constant diameter being such that said at least one rod cannot rotate about said longitudinal axis when said attachment element is secured on said at least one rod and said at least one rod is between the two pins at said respective portions of constant diameter.

14. A device according to claim 1, wherein the bridge further comprises, on a side of the bridge opposite the side contacting said at least one rod, abutting projections having vertebra contact surfaces.

15. A device according to claim 1, wherein said at least one rod is made of material with a shape memory.

16. A method of attaching a rod to a spinal column comprising the steps of:
    (a) hooking two hooks to a vertebra arch;
    (b) mounting a bridge for interconnecting said hooks;
    (c) fixing said bridge and hooks to a vertebra;
    (d) inserting a rod connector into said bridge; and
    (e) inserting the rod through said rod connector, said two hooks extending substantially perpendicular to the rod.

17. The method as recited in claim 16, further comprising the steps of rotating said rod within said rod connector until a desired position is achieved, and clamping said rod connector to prevent the rod from rotating.

18. The method as recited in claim 16, further comprising repeating steps (a)–(d) for a number of vertebra.

19. The method as recited in claim 16, wherein said hooks each comprise two detachably interconnected members, a first member being a stud and a second member being hook-shaped, said step (a) further comprises mounting said second member on said vertebra and step (b) further comprises inserting said first member through slotted holes of said bridge and into a threaded throughbore in said second member, displacing said hooks towards and away from each other, and fixing said hooks on said bridge.

* * * * *